(12) United States Patent
Burkett et al.

(10) Patent No.: US 6,733,819 B2
(45) Date of Patent: *May 11, 2004

(54) METHOD AND APPARATUS FOR POLYMER APPLICATION TO INTRACORPOREAL DEVICE

(75) Inventors: David Burkett, Temecula, CA (US); Emmanuel Biagtan, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/452,614

(22) Filed: Jun. 2, 2003

(65) Prior Publication Data

US 2003/0198733 A1 Oct. 23, 2003

Related U.S. Application Data

(60) Continuation of application No. 10/161,786, filed on Jun. 4, 2002, now Pat. No. 6,599,557, which is a division of application No. 09/441,695, filed on Nov. 16, 1999, now Pat. No. 6,419,745.

(51) Int. Cl.$^7$ ............................. B05D 1/18; B05D 3/12
(52) U.S. Cl. .................. 427/2.1; 427/2.24; 427/358; 427/434.2; 427/434.4; 427/434.6
(58) Field of Search .................. 427/2.1, 224, 358, 427/356, 430.1, 434.2, 434.21, 434.6

(56) References Cited

U.S. PATENT DOCUMENTS

| | | | |
|---|---|---|---|
| 233,970 A | 11/1880 | Berthoud et al. | |
| 2,561,569 A | 7/1951 | Flynn | |
| 3,694,131 A | 9/1972 | Stuart | |
| 4,106,506 A | 8/1978 | Koehn et al. | |
| 5,240,537 A | 8/1993 | Bodicky | |
| 5,358,570 A | 10/1994 | Drawbaugh | |
| 5,409,644 A | 4/1995 | Martin et al. | |
| 5,447,793 A | 9/1995 | Montsinger | |
| 5,465,733 A | * 11/1995 | Hinohara et al. | |
| 6,042,876 A | 3/2000 | Deem | |
| 6,280,788 B1 | 8/2001 | Rakhorst et al. | |
| 6,599,557 B2 | * 7/2003 | Burkett et al. | |

FOREIGN PATENT DOCUMENTS

JP 60-110422 6/1985

* cited by examiner

*Primary Examiner*—Michael Barr
(74) *Attorney, Agent, or Firm*—Fulwider Patton Lee & Utecht, LLP

(57) ABSTRACT

A method and apparatus for applying a polymer coating on an elongated substrate, preferably an elongate intracorporeal device in the form of a guidewire. An extrudable polymer cartridge is moved by a cartridge advancement mechanism into a guide chamber which is heated at an end with a die or orifice through which a desired portion of a guidewire may pass and be coated. Parameters such as guide chamber temperature, pull speed and force exerted by the cartridge advancement mechanism may be controlled with a computer program in order to achieve repeatable results. The guide chamber, extrudable polymer cartridge, die, and push tube may all be made from polymer components which can be reused or disposed of after a single use. The extrudable polymer cartridge may have a variety of configurations including multiple layers of different materials, eccentric shapes, multiple lumens for multiple elements to be drawn through and coated and asymmetric disposition of different materials with respect to the longitudinal axis as viewed in a transverse cross section which can give bending properties having a preferred direction in the coated guidewire or device.

20 Claims, 8 Drawing Sheets

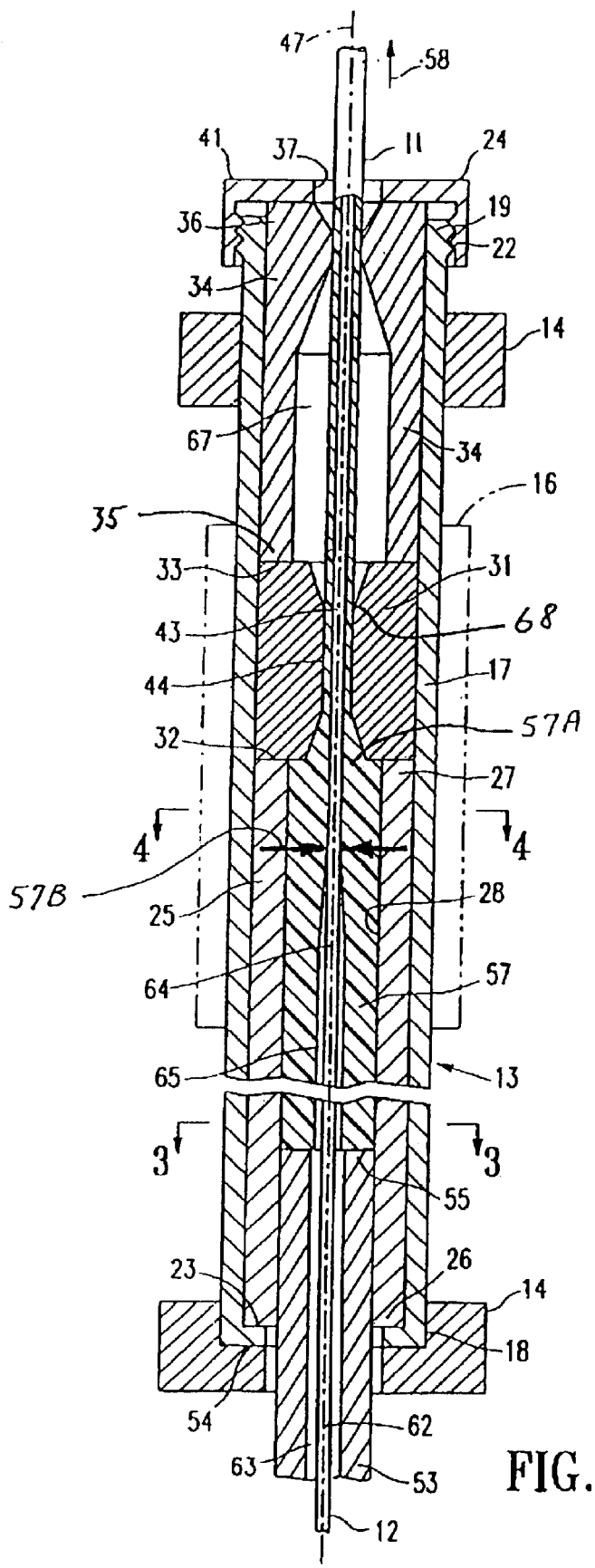
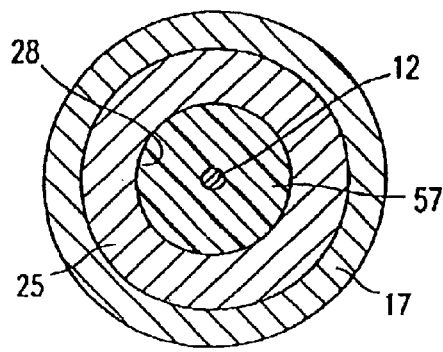
FIG. 4
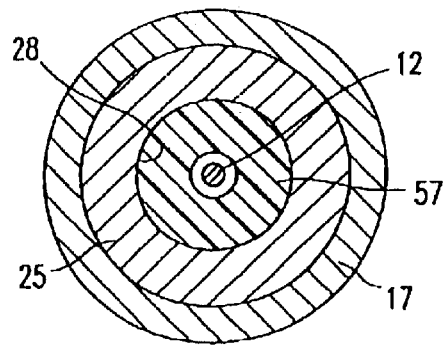
FIG. 3
FIG. 2

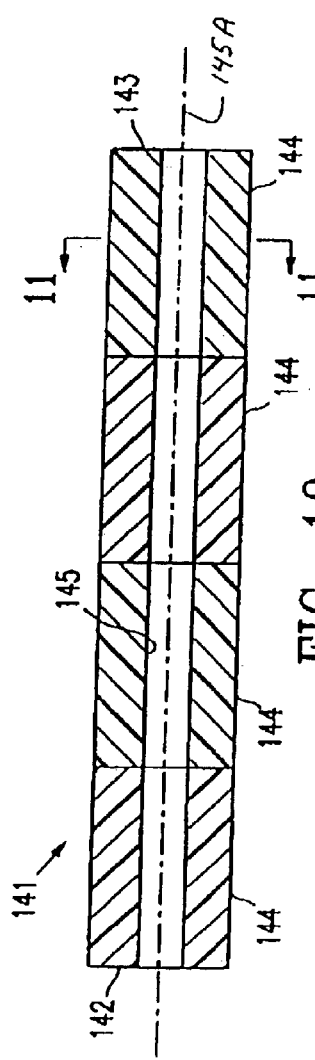
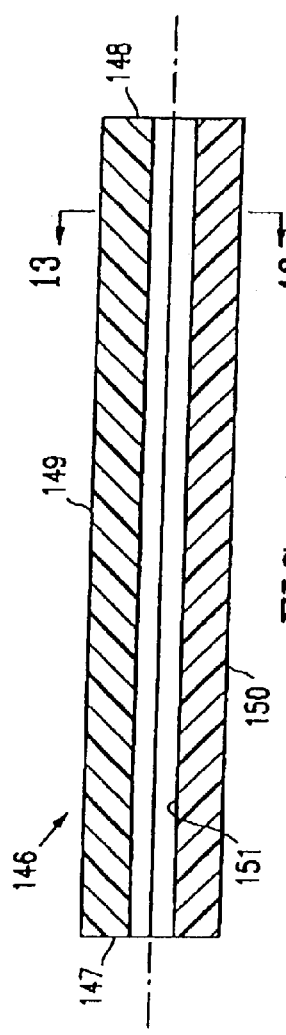
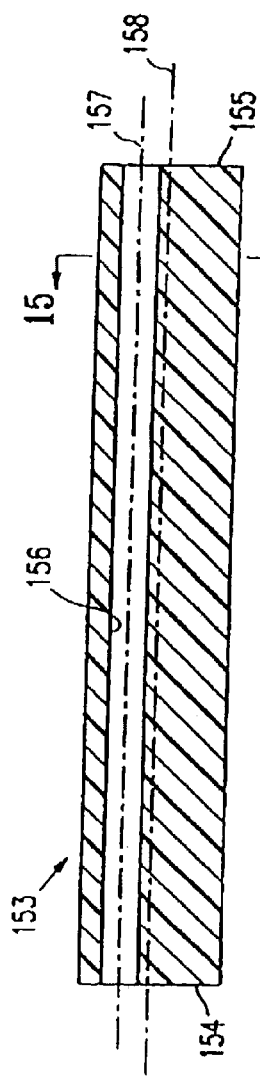
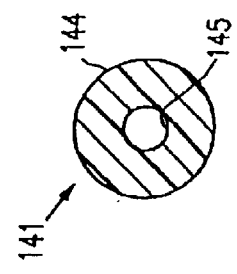
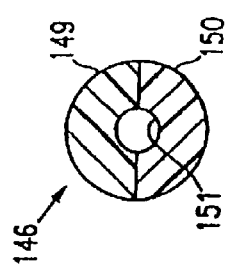
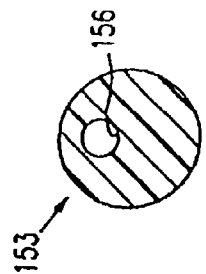

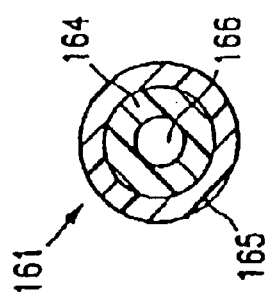
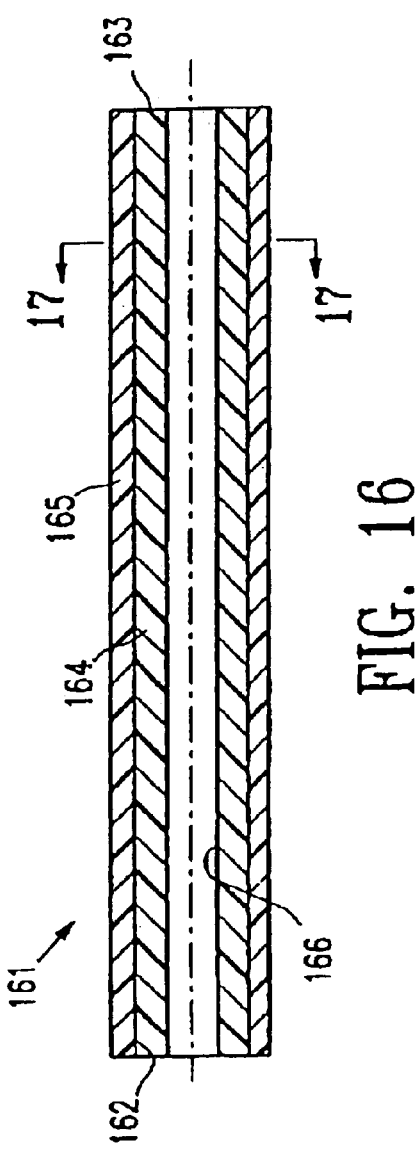
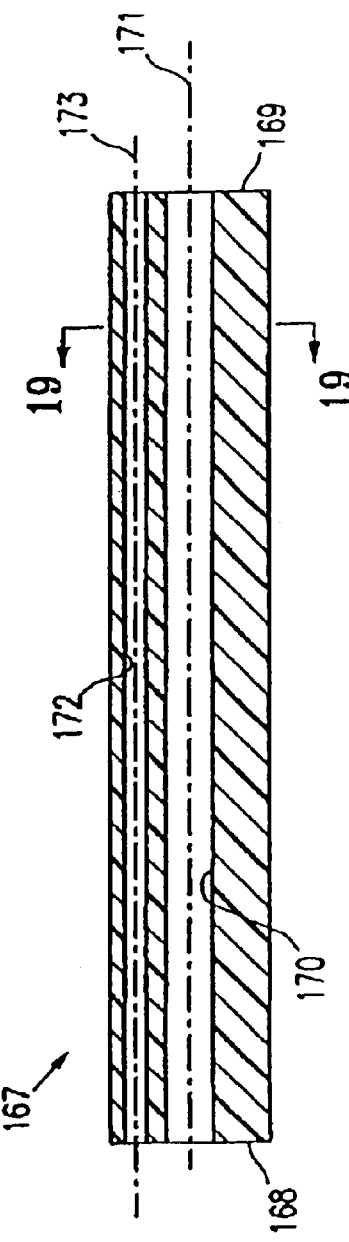

METHOD AND APPARATUS FOR POLYMER APPLICATION TO INTRACORPOREAL DEVICE

CROSS-REFERENCE TO RELATED APPLICATIONS

This is a continuation application of a application having U.S. Ser. No. 10/161,786, filed Jun. 4, 2002 now U.S. Pat No. 6,599,557, which is a divisional of U.S. Ser. No. 09/441,695 filed Nov. 16, 1999, now U.S. Pat. No. 6,419,745 B1 issued Jul. 16, 2002, the contents of all of which are hereby incorporated by reference.

BACKGROUND

This invention relates to an apparatus and method for applying a polymer coating to a desired length of an elongate member, preferably to an elongate intracorporeal device. More specifically, the invention relates to a method and apparatus for applying a polymer coating to a desired length of an intracorporeal guiding device or guidewire. The invention can also be used to apply a polymer coating to a length of any other suitable device such as a vascular stent, cardiac pacing leads, catheter tubings, braided or solid electrical wire, coaxial cable or the like.

In a typical prior art process for applying a polymer coating over an elongate member, an extrusion machine is used which has a heated die head with channels leading to a heated chamber within the die head. Melted polymer is forced into the chamber with a lead screw which forces solid polymer, usually in the form of pellets, into the heated chamber. The elongate member to be coated is passed through the back end of the die head into the chamber and out of an orifice in an extrusion die which is attached to the extrusion head. The elongate member is then pulled through the die as melted polymer is forced into the die head and onto the elongate member. Normally, the orifice in the die will be larger than the elongate member so that a desired amount of the melted polymer remains on the elongate member after passing through the orifice. After passing through the orifice, the melted polymer on the elongate device cools and the coating process is complete.

A prior art process such as that described above is well suited in many cases for coating long lengths of durable elongated members or substrate. The equipment used is large, expensive and cumbersome and can damage a fragile substrate being pulled through the device, such as a guidewire distal section with a small diameter helical coil. In addition, the amount of effort and expense required for a given set up often does not justify small runs of material. Also, the equipment is not Nell suited for coating short lengths of discrete elongated members, such as guidewires or the like, because adjusting the settings to achieve desired coating dimensions and parameters is usually a process that requires several minutes of running time in order for equilibrium of the dynamic to be established and stabilization of the process to occur. This often requires running many feet of substrate through the die head prior to stabilization which is not possible with a guidewire which is only several feet long.

Another difficulty exists in trying to vary the coating parameters dynamically in a controlled fashion in order to achieve a coating which has varying parameters such as a transverse dimension along an axial direction. As mentioned above, the usual coating equipment of the prior art is large and cumbersome and it is impractical to vary parameters such as temperature of the die, speed of pull, and pressure exerted on the melted polymer over short lengths of an elongate member substrate.

What has been needed is an apparatus suitable for applying a variety of polymer coatings to a discrete length of a fragile intracorporeal device substrate with quick response time for variation in extrusion parameters. What has also been needed is an apparatus suitable for coating an elongate intracorporeal member that has automatable control of extrusion parameters such as die temperature, pull speed and pressure applied to melted polymer which can produce repeatable control of diameter and other dimensions of the polymer coating applied. In addition, it is desirable to have an apparatus suitable for reliably applying a polymer coating with a constant outer transverse dimension to a substrate which varies in transverse dimension or diameter along its axial length.

SUMMARY

The invention is directed to an apparatus for applying a polymer coating to an elongate intracorporeal device, specifically, a guidewire. In one embodiment, the apparatus can have a guide chamber with an input end having an input port and an output end. An extrusion orifice is disposed at the output end of the guide chamber and is in fluid communication with the guide chamber. The extrusion orifice can be configured to allow an elongate intracorporeal device or other substrate to pass through or be pulled through the extrusion orifice with a desired thickness or configuration of polymer coating on the elongate intracorporeal device or substrate. The orifice can be configured to leave a fixed thickness of polymer over the elongate intracorporeal device, or the orifice can be shaped so as to leave a desired profile or configuration of polymer coating on the device, e.g., an orifice having an oval, square or triangular cross section.

A heater member is disposed in thermal communication with the guide chamber and serves to heat a desired portion of the guide chamber. A cartridge advancement mechanism is disposed adjacent the guide chamber. In use, an extrudable polymer cartridge is placed within the guide chamber of the apparatus. The cartridge advancement mechanism can be configured to axially translate the extrudable polymer cartridge into the guide chamber in a direction of extrusion, i.e., a direction from the input end of the guide chamber to the output end of the guide chamber. The extrudable polymer cartridge can have a lumen extending longitudinally through the cartridge with the lumen being sized or configured to accept the elongate intracorporeal device. The lumen of the extrudable polymer cartridge is typically sized to allow the elongate intracorporeal member to slide freely within the lumen.

In another embodiment, a guide chamber is formed by a guide tube with the guide chamber being disposed within the guide tube. The guide tube has an input end with an input port in fluid communication with the guide chamber and an output end. A die having an extrusion orifice is disposed at the output end of the guide tube such that the extrusion orifice is in fluid communication with the guide chamber. The extrusion orifice of the die can be configured to allow an elongate intracorporeal device to pass through the die with a desired configuration of polymer coating on the member. A heater member is disposed in thermal communication with the guide tube for heating a desired portion of the guide tube or die.

A push tube is disposed at least partially and slidably within the guide chamber. The push tube has a contact end, an attachment end, a longitudinal axis and at least one inner lumen extending substantially parallel to the longitudinal axis of the push tube. The inner lumen of the push tube is configured to accept a desired elongate intracorporeal device. In use, an extrudable polymer cartridge, having similar properties to the extrudable polymer cartridge discussed above, can be disposed within the guide chamber between the extrusion orifice of the die and the contact end of the push tube.

In another embodiment, a puller is disposed adjacent the output end of the guide tube. The puller can be configured to be temporarily secured to a desired portion of the elongate intracorporeal device and apply a force and movement in the direction of extrusion on the device. A push tube actuator is disposed adjacent the input end of the guide tube and is configured to apply a force and movement on the extrudable polymer cartridge disposed within the guide chamber. Specifically, the push tube is disposed between the extrudable polymer cartridge and the push tube actuator and mechanically couples the push tube actuator to the extrudable polymer cartridge. A computing machine may be electronically connected to a temperature sensor coupled to the heater member, the puller and the push tube actuator. The computing machine can be used to repeatably control the temperature of the heating member, the rate of axial movement of the elongate intracorporeal device in a direction of extrusion by controlling the rate of axial movement of the puller, and the rate of feed or axial movement in the direction of extrusion of the extrudable polymer cartridge by controlling the rate of movement or force applied to the push tube in the direction of extrusion.

One of the advantages of the apparatus for applying a polymer coating is that many of the components of the apparatus can be manufactured from disposable polymer materials that are made to be modular and avoid the need for cleaning of components. For example, both the guide tube and the die can be made from a variety of high temperature polymers such as polyimide (PI), polytetraflouroethylene (PTFE), liquid crystal polymer (LCP) and polyetheretherkeytone (PEEK) This allows a subassembly consisting of the guide tube, die and extrudable polymer cartridge to be loaded into a corresponding guide tube assembly for each elongate intracorporeal device to be coated. When the device has been coated, the subassembly can be disposed of and a new subassembly loaded into the guide tube assembly. This eliminates the need for time consuming cleaning operations and allows the use of varying die configurations and extrudable polymer cartridge materials from one elongate intracorporeal device to the next.

Another advantage of the apparatus for applying a polymer coating is the ability to reliably maintain concentricity of the coating applied to the elongate intracorporeal device. Where such concentricity is desired, the use of an extrudable polymer cartridge having an inner lumen which is concentric to a longitudinal axis of the cartridge provides centering of the elongate intracorporeal device prior to passing through the extrusion orifice. As the extrudable polymer cartridge is melted at the output end of the guide chamber and applied to the elongate intracorporeal device, the unmelted portion of the cartridge immediately adjacent a melt zone of the extrudable polymer cartridge continuously provides centering of the elongate intracorporeal device within the guide chamber and extrusion orifice. Also, the melted portion of the extrudable polymer cartridge at the melt zone can be applied evenly in a radially inward direction from all sides of the elongate intracorporeal device in embodiments of the invention where the inner lumen of the extrudable polymer cartridge is concentric with the longitudinal axis of the cartridge. This can also facilitate maintaining concentricity of the polymer coating.

In use, an extrudable polymer cartridge is placed in the guide chamber of the guide tube between the extrusion orifice and the contact end of the push tube. An elongate intracorporeal device is loaded into the die, at least of a portion of the inner lumen of the extrudable polymer cartridge and optionally the inner lumen of the push tube. The elongate intracorporeal device is then temporarily secured to the puller and the heater member activated. When the portion of the extrudable polymer cartridge adjacent the die attains a desired temperature and viscosity, the puller and cartridge advancement mechanism, typically consisting of a push tube actuator, are activated. This advances both the elongate intracorporeal device and extrudable polymer cartridge in the direction of extrusion, i.e. in a direction from the input end of the guide chamber to the output end of the guide chamber.

The coating process can be terminated in several ways. The process may be terminated when an end or extremity of the elongate intracorporeal device is drawn through the output end of the guide chamber and die. This method will typically coat the entire end or extremity of the elongate intracorporeal device. Alternatively, the advancement of the extrudable polymer cartridge can be stopped by deactivating the cartridge advancement mechanism while continuing to advance the elongate intracorporeal device in the direction of extrusion. In this way, the melted extrudable polymer cartridge is no longer feeding into the extrusion orifice and coating the elongate intracorporeal device. Also, the amount of material in the extrudable polymer cartridge may be limited to suffice for coating only a desired portion of an elongate intracorporeal device. As the extrudable polymer cartridge is advanced in the direction of extrusion and polymer coating is applied, the cartridge gets shorter. The process continues until the contact end of the push tube hits the die and melted polymer material is no longer fed into the extrusion orifice and the coating process stops, although the elongate intracorporeal may continue to be pulled or advanced in the direction of extrusion.

BRIEF DESCRIPTION OF THE DRAWINGS

FIG. 2 is an elevational view in partial section of the guide tube assembly shown in FIG. 1 taken along lines 2—2 in FIG. 1.

FIG. 3 is a transverse cross sectional view of the guide tube assembly shown in FIG. 2 taken along lines 3—3 in FIG. 2.

FIG. 4 is a transverse cross sectional view of the guide tube assembly shown in FIG. 2 taken along lines 4—4 in FIG. 2.

FIG. 10 illustrates an extrudable polymer cartridge having features of the invention.

FIG. 11 is a transverse cross sectional view of the extrudable polymer cartridge of FIG. 10 taken along lines 11—11 in FIG. 10.

FIG. 12 illustrates an extrudable polymer cartridge having features of the invention.

FIG. 13 is a transverse cross sectional view of the extrudable polymer cartridge of FIG. 12 taken along lines 13—13 in FIG. 12.

FIG. 14 illustrates an extrudable polymer cartridge having features of the invention.

FIG. 15 is a transverse cross sectional view of the extrudable polymer cartridge of FIG. 14 taken along lines 15—15 in FIG. 14.

FIG. 16 illustrates an extrudable polymer cartridge having features of the invention.

FIG. 17 is a transverse cross sectional view of the extrudable polymer cartridge of FIG. 16 taken along lines 17—17 in FIG. 16.

FIG. 18 illustrates an extrudable polymer cartridge having features of the invention.

FIG. 19 is a transverse cross sectional view of the extrudable polymer cartridge of FIG. 18 taken along lines 19—19 in FIG. 18.

DETAILED DESCRIPTION

Figure 1:
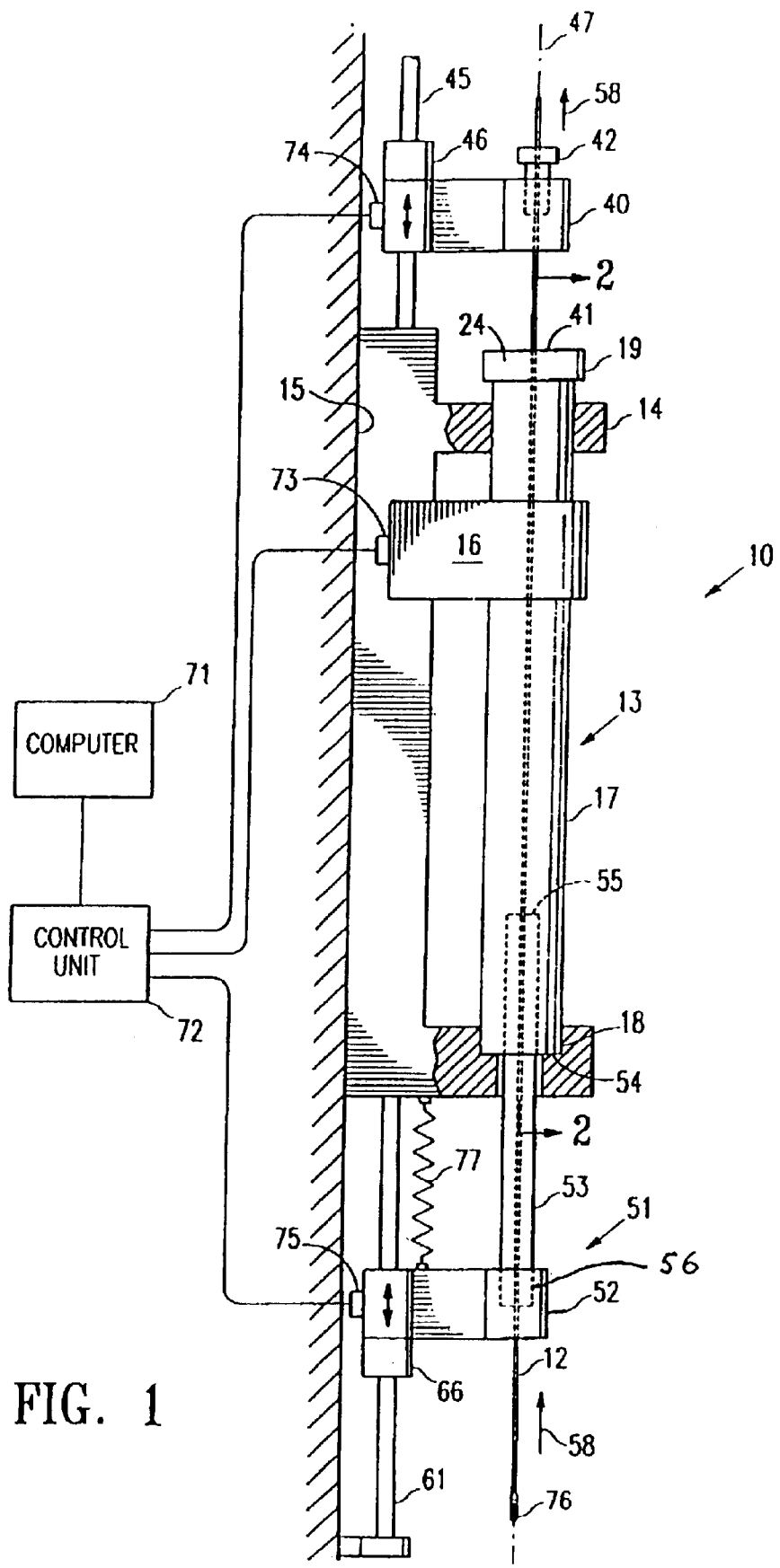
FIG. 1 is an elevational view in partial section of an apparatus for applying a polymer coating to an elongate intracorporeal device having features of the invention.

FIGS. 1–4 illustrate a polymer coating apparatus 10 for applying a polymer coating 11 to an elongate intracorporeal device 12. A guide tube assembly 13 is removably secured to a guide tube assembly mount 14. The guide tube assembly mount 14 is secured to a mounting surface 15, which can be an even vertical surface, but which can have any desired configuration or orientation. A heater member 16 is secured in thermal communication with a guide tube housing 17 of the guide tube assembly 13 and serves to supply heat energy to a desired portion of the guide tube assembly 13. The guide tube assembly 13 includes a guide tube housing 17 which has an input end 18 and an output end 19. The output end 19 has a threaded portion 22 and the input end 18 has a retainer lip 23. A retainer cap 24 is threaded onto the threaded portion 22 of the output end 19 of the guide tube housing 17.

The guide tube housing 17 can be made of a conductive material such as stainless steel, a machineable insulative material such as Vespel® or any other suitable material. A guide tube 25 having an input end 26, an output end 27 and a guide chamber 28 disposed within the guide tube 25 is disposed within the guide tube housing 17. The input end 26 of the guide tube 25 is disposed against the retainer lip 23 of the guide tube housing 17. A die 31 having an input end 32 and an output end 33 is disposed within the guide tube housing 17 with the input end 32 of the die 31 against the output end 27 of the guide tube 25. An optional centering insert 34 having an input end 35 and an output end 36 is disposed within the guide tube housing 17 with the input end 35 of the centering insert 34 against the output end 33 of the die 31. The retainer cap 24 with a center hole 37 is threaded onto the threaded portion 22 of the guide tube housing 17 to hold the guide tube 25, die and centering insert 34 within the guide tube housing 17.

In one embodiment, the guide tube 25 has a length of about 0.5 to about 5 inch, specifically about 1.0 to about 3.0 inch. The guide tube 25, die 31 and centering insert 34 can have an outer diameter of about 0.03 to about 0.2 inch, specifically about 0.05 to about 0.1 inch. The guide tube 25 of the embodiment can have a wall thickness of about 0.005 to about 0.015 inch. In other embodiments, the length, outer diameter and wall thickness of the guide tube 25 can vary significantly from the dimensions given above to suit the desired application. The guide tube 25, die 31 and centering insert 34 can be disposable and made from a high temperature polymer such as PI, PTFE, LCP or PEEK.

As best shown in FIG. 1, a puller 40 is disposed adjacent an output end 41 of the guide tube assembly 13 and has a clamp 42 aligned with the longitudinal axis 43 of an inner lumen 44 of the die 31 for temporarily securing the elongate intracorporeal device 12 to the puller 40. The clamp 42 temporarily secures a desired portion of the elongate intracorporeal device 12 to the puller 40 such that the elongate intracorporeal device 12 is centered within the inner lumen 44 of the die 31. The puller 40 is slidably disposed on a puller track 45 and has motor 46 which mechanically engages the puller track 45 and moves the puller 40 parallel to a longitudinal axis 47 of the guide tube assembly 13.

A cartridge advancement mechanism 51 consisting of a push tube actuator 52 and a push tube 53 is disposed adjacent an input end 54 of the guide tube assembly 13. The push tube actuator 52 is mechanically coupled to the push tube 53 with the push tube 53 having a contact end 55 and an actuator end 56. The push tube 53 is configured to have the contact end 55 slidably disposed within the guide chamber 28 of the guide tube 25 and apply force to an extrudable polymer cartridge 57 disposed within the guide chamber 28 in a direction of extrusion. The direction of extrusion is defined to be from the input end 54 of the guide tube assembly 13 to the output end 41 of the guide tube assembly 13 as indicated by arrows 58.

The push tube actuator 52 is slidably disposed on a push tube actuator track 61 such that a longitudinal axis 62 of an inner lumen 63 of the push tube 53 is aligned with the longitudinal axis 43 of the die 31 and longitudinal axis 64 of an inner lumen 65 of the extrudable polymer cartridge 57. A push tube actuator motor 66 is disposed on the push tube actuator 52 and mechanically coupled to the push tube actuator track 61 so as to enable the motor 66 to axially translate the push tube actuator 52 on the push tube actuator track 61 along a longitudinal axis 47 of the guide tube assembly 13.

The elongate intracorporeal device 12 is disposed within an inner lumen 67 of the centering insert 34, the extrusion orifice 68 of the die 31, the inner lumen 65 of the extrudable polymer cartridge 57 and the inner lumen 63 of the push tube 53. The elongate intracorporeal device 12 is also shown as being disposed along the longitudinal axis 47 of the guide tube assembly 13. Other configurations may be used where the elongate intracorporeal device 12 is offset from the longitudinal axis 47 of the guide tube assembly 13.

A computer 71 is in electrical communication with an electronic control unit 72 which is in electrical communication with a temperature sensor 73 disposed in thermal communication with the heater member 16, a puller position indicator 74 disposed on the puller 40, and a push tube actuator position indicator 75 disposed on the push tube actuator 52. The temperature sensor 73 provides an electrical signal to the computer 71 indicating the temperature of the heater member 16. The puller position indicator 74 provides an electrical signal to the computer 71 indicating the position of the puller 40 relative to the output end 41 of the guide tube assembly 13. The push tube actuator position indicator 75 provides an electrical signal to the computer 71 indicating the position of the push tube actuator 52 relative to the input end 54 of the guide tube assembly 13. In addition, the computer 71 is electrically coupled to the control unit 72 such that a signal from the computer 71 can control the amount of power to the heater member 16, the speed and direction of translation of the puller 40 and the speed and direction of translation of the push tube actuator 52.

In this way, the computer 71 can be programmed to repeatably control the temperature of the heater member 16, the rate of pull of the elongate intracorporeal device 12 through the guide tube assembly 13 and the rate of feed of the extrudable polymer cartridge 57 into the guide chamber 28 in the direction of extrusion. This enables the computer 71 to repeatably control the entire coating process for consistent coating results. The computer 71 may be a standard personal computer, or any suitable substitute such as a custom integrated circuit or the like. In addition, the function of the computer 71 could be carried out with standard analog circuitry of suitable configuration that would provide a desired and repeatable heater member 16 temperature, rate of pull of the puller 40 and rate of feed of the push tube actuator 52.

In use, the retainer cap 24 is removed from the guide tube housing 17. The guide tube 25 is loaded into the guide tube housing 17 from the output end 19 of the guide tube housing 17 until the input end 26 of the guide tube 25 contacts the retainer lip 23 of the guide tube housing 17 and the contact end 55 of the push tube 53 enters the guide tube chamber 28 at the input end of the guide tube 25. The extrudable polymer cartridge 57 is then loaded into the guide chamber 28 at the output end of the guide tube 25 until it contacts the contact end 55 of the push tube 53. Next, the die 31 is loaded into the guide tube housing 17 with the input end 32 of the die 31 adjacent the output end 27 of the guide tube 25. The centering insert 34 is then loaded into the guide tube housing 17 with the input end 35 of the centering insert 34 adjacent the output end 33 of the die 31. The retainer cap 24 is then replaced which confines the guide tube 25, extrudable polymer cartridge 57, die 31 and centering insert 34 within the guide tube housing 17.

The elongate intracorporeal device 12 is then inserted through the inner lumen 67 of the centering insert 34, the extrusion orifice 68 and inner lumen 44 of the die, the inner lumen 65 of the extrudable polymer cartridge 57, and at least a portion of the inner lumen 63 of the push tube 53. The elongate intracorporeal device 12 is then temporarily secured to the puller 40 by the clamp 42. The coating cycle is then started by supplying power to the heater member 16 which heats a desired portion of the die 31, guide tube 25 and extrudable polymer cartridge 57 which are adjacent and in thermal communication with the heater member 16.

Thermal energy from the heater member 16 may be coupled to the die 31 alone, the die 31 and the output end 27 of the guide tube 25 or the die 31 and any desired portion of the guide tube 25. Also, it may be useful in some embodiments to generate a temperature gradient along the centering insert 34, die 31 and guide tube 25. In one embodiment, it is preferable to concentrate most of the thermal energy on the die 31 and output end 27 of the guide tube 25.

As thermal energy is transferred to the extrudable polymer cartridge 57, it can begin to soften or melt at a melt zone 57A. When the portion of the extrudable polymer cartridge 57 adjacent the die 31 approaches a desired temperature or viscosity or both, force in the direction of extrusion is applied to the extrudable polymer cartridge 57. This pushes the melted or softened polymer material in the melt zone 57A of the extrudable polymer cartridge 57 into the input end 32 and inner lumen 44 of the die 31 and onto the elongate intracorporeal device 12. When the force in the direction of extrusion is initiated on the extrudable polymer cartridge 57, the elongate intracorporeal device 12 is simultaneously advanced in the direction of extrusion so that as the extrudable polymer cartridge 57 is heated, melted, and forced into the die 31. The melted extrudable polymer cartridge 57 is applied to the moving elongate intracorporeal device 12 in a radially inward direction as indicated by arrows 57B. As shown in FIG. 2, the extrudable polymer cartridge 57 is applied evenly at the melt zone 57A from all directions as indicated by arrows 57B. The evenly distributed inward radial force helps maintain the concentricity of the polymer coating 11 if the lumen of the extrudable polymer cartridge is concentric with the longitudinal axis 64 of the extrudable polymer cartridge 57 and longitudinal axis 43 of the die 31. The coating process is carried out continuously until a desired portion of the elongate intracorporeal device 12 has been coated. The process may be terminated by exhaustion of the extrudable polymer cartridge 57, cessation of the force in the direction of extrusion on the extrudable polymer cartridge, or passage of an extremity 76 of the elongate intracorporeal device 12 through the die 31.

In the embodiment of the polymer coating apparatus 10 shown in FIGS. 1–4, the force in the direction of extrusion on the extrudable polymer cartridge 57 is applied by the contact end 55 of the push tube 53 which is mechanically coupled to the push tube actuator 52. One alternative to using push tube actuator motor 66 to apply force and motion to the push tube actuator 52 is to apply a substantially constant force in the direction of extrusion on the push tube actuator 52 with an optional constant force spring 77. The constant force spring 77 may be secured to any suitable portion of the push tube 53, push tube actuator 52, guide tube assembly mount 14, or mounting surface 15. A suitable trigger mechanism can be used to initiate the force from the constant force spring 77 in the direction of extrusion at the appropriate time in the coating cycle.

When the coating cycle is finished, the elongate intracorporeal device 12 is removed from the guide tube assembly 13 and the puller 40. The retainer cap 24 of the guide tube housing 17 is removed as well as the spent die 31, centering insert 34, guide tube 25 and extrudable polymer cartridge 57. The push tube 53 is then reset to its original position and a new guide tube 25, extrudable polymer cartridge 57, die 31 and centering insert 34 loaded into the guide tube housing 17. It may be possible to reuse the die 31, guide tube 25 or centering insert 34. Also, the new guide tube 25, die 31 and extrudable polymer cartridge 57 may be loaded into the guide tube housing 17 in one connected modular unit or subassembly in order to lessen the time between coating cycles.

The temperature range of the heater member 16, die 31 and desired portion of the guide tube 25 used for the process of the polymer coating apparatus 10 can vary significantly depending on the desired result, size and material composition of the elongate intracorporeal device 12 and material composition of the extrudable polymer cartridge 57. For coating an elongate intracorporeal device 12 consisting of a guidewire, in order to yield a finished outer diameter of about 0.012 to about 0.016 inch, a temperature range of about 340 to about 390 degrees Fahrenheit, specifically about 350 to about 380 degrees Fahrenheit is typical if using polyurethane for the extrudable polymer cartridge 57 material.

As the temperature of the heater member 16 is changing as the coating process is started, it may be desirable to trigger axial movement of the elongate intracorporeal device 12 in the direction of extrusion just prior to reaching the desired target temperature. For example, if the ultimate target temperature of the heater member 16 is about 365 degrees Fahrenheit, then the puller 40 may be triggered by programming of the computer 71 to start the puller 40 moving in the direction of extrusion when the heater member 16 reaches a temperature of about 362 degrees Fahrenheit.

The rate of speed of pull of the elongate intracorporeal device 12 through the guide tube assembly 13 can vary considerably depending on many factors including the size and durability of the elongate intracorporeal device 12, the temperature of the heater member 16 and the material of the extrudable polymer cartridge 57. For the example given above, with an elongate intracorporeal device 12 of stainless steel having a desired finish outer diameter of about 0.012 to about 0.016 inch, using polyurethane for the extrudable polymer cartridge 57, a typical rate of pull can be from about 0.25 to about 1.0 cm/second for durable portions of the member 12, and about 0.05 to about 0.15 cm/second for more fragile portions of the member 12, such as portions of the elongate intracorporeal device 12 covered by a helical coil which is subject to mechanical deformation. In one embodiment, the force applied to the extrudable polymer cartridge 57 by the push tube 53 via the push tube actuator 52 can be from about 0.5 to about 10 pounds, specifically about 1.0 to about 2.0 pounds.

In another embodiment, the cartridge advancement mechanism 51, described above as consisting of a push tube actuator 52 coupled to a push tube 53 can be replaced with a substantially constant force spring coupled to the push tube so as to apply a substantially constant force in the direction of extrusion on the extrudable polymer cartridge 57 during the coating process. The amount of force can be similar to the forces noted above with regard to the push tube actuator 52 embodiment.

Figure 5:
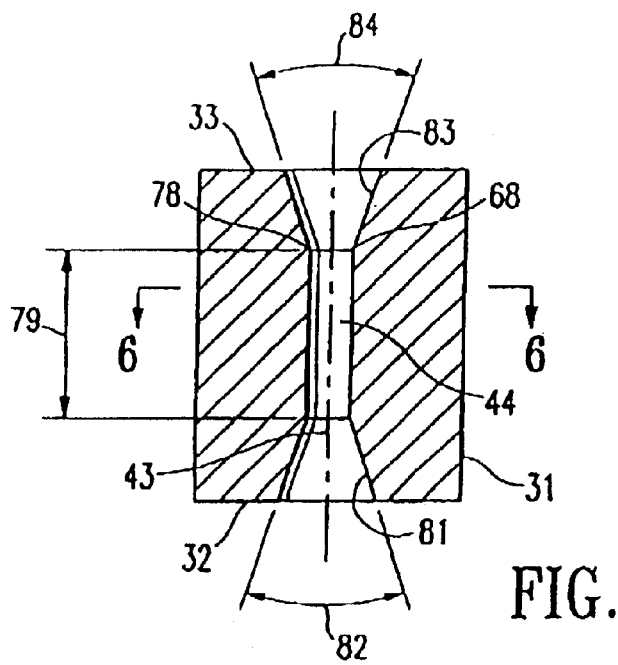
FIG. 5 is an elevational view in longitudinal cross section of the die in the guide tube assembly shown in FIGS. 1–4, having features of the invention
Figure 6A:
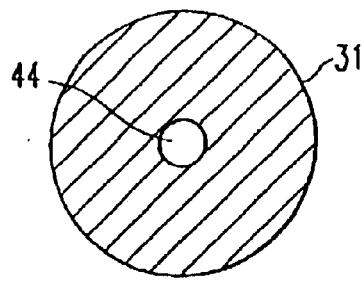
FIGS. 6A–6C are transverse cross sectional views of the die shown in FIG. 5 taken along lines 6—6 in FIG. 5, having various extrusion orifice configurations.
Figure 6B:
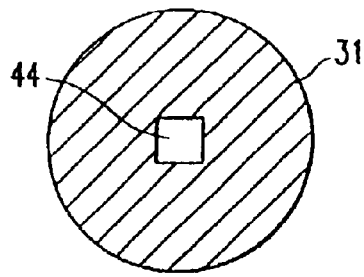
Figure 6C:
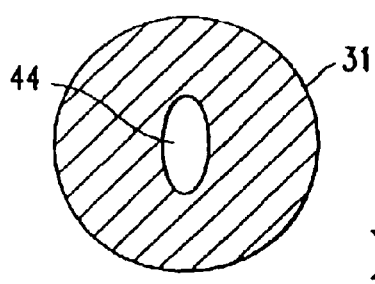

FIGS. 5–6C illustrate an enlarged view of the embodiment of the die 31 shown in FIGS. 2 and 4. The die 31 can be made from a variety of materials, including high temperature polymers such as PI, PTFE, LCP and PEEK. The die 31 can also be made from metal or any other suitable material The die 31 has an input end 32, an output end 33 and an inner lumen 44. An extrusion orifice 68 is disposed at an output extremity 78 of the inner lumen 44. The length 79 of the inner lumen 44 of the die 31 can vary significantly depending on the desired result and numerous other factors. In one embodiment, the length of the inner lumen 44 can range from about 0.02 to about 0.5 inch, specifically about 0.05 to about 0.08 inch. A transverse dimension of the inner lumen 44 and extrusion orifice 68 of the die 31 in said embodiment can be from about 0.01 to about 0.25 inch, specifically about 0.011 to about 0.015 inch.

The die 31 has an outer transverse dimension similar to an outer transverse dimension of the guide tube 25. An input taper 81 at the input end 32 of the die 31 has an input taper angle 82. An optional output taper 83 at the output end 33 of the die 31 has an output taper angle 84. Output taper angle 84 and input taper angle 82 can be from about 15 degrees to about 180 degrees, i.e. a flat cut end with no taper, specifically, from about 35 to about 45 degrees, and more specifically, from about 36 to about 40 degrees. Although the extrusion orifice 68 of the die 31 shown in FIG. 5 has a round cross section as shown in FIG. 6A, the cross section of the extrusion orifice 68 can have any desired configuration or shape such as the square configuration shown in FIG. 6B or the elliptical configuration shown in FIG. 6C. Any other suitable extrusion orifice 68 configuration or cross sectional shape can be used to achieve a desired result.

Figure 7:
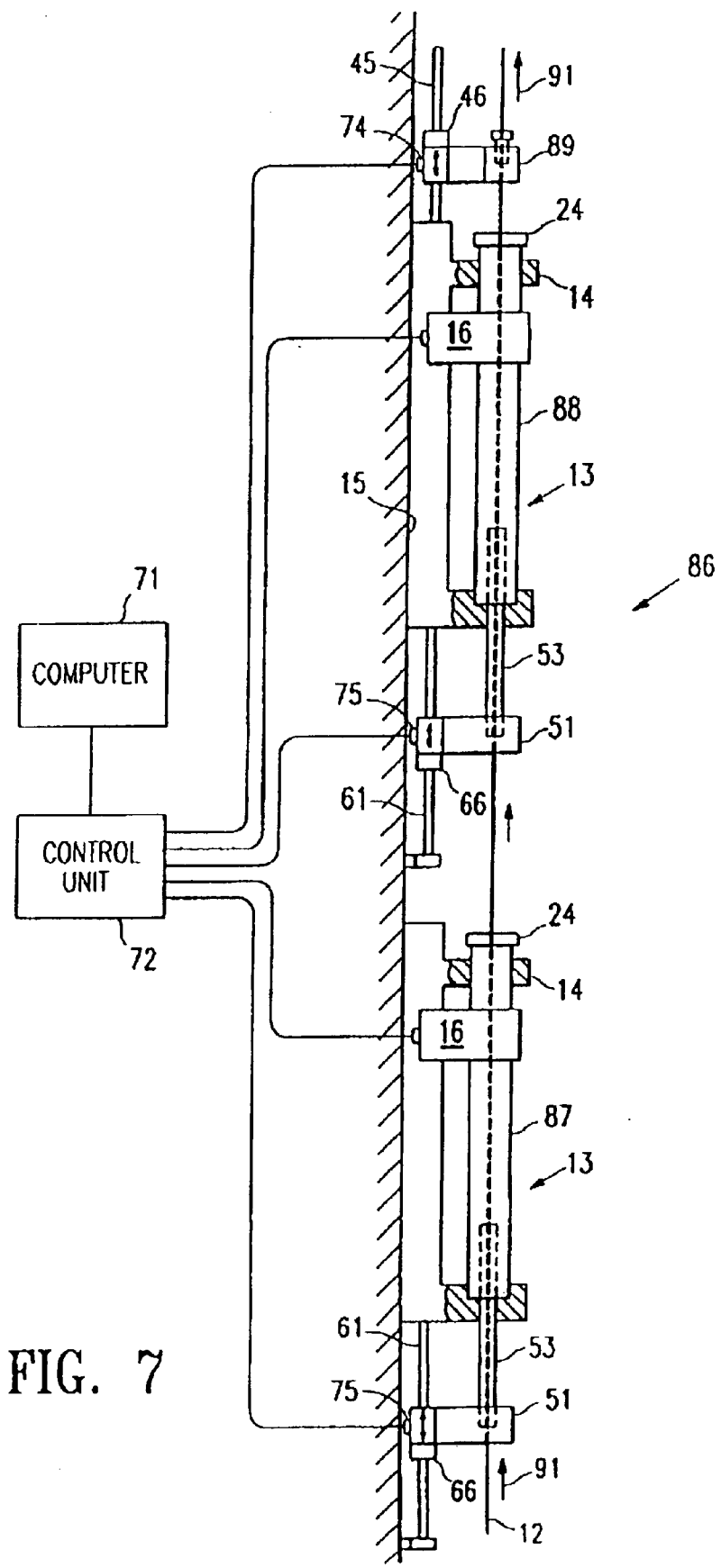
FIG. 7 is an elevational view in partial section of a tandem apparatus for applying a polymer coating to an elongate intracorporeal device having features of the invention.

FIG. 7 illustrates a tandem polymer coating apparatus 86 having a first polymer coating apparatus 87 in line with a second polymer coating apparatus 88. The various components of the first and second polymer coating apparatus 87 and 88 can have components similar to the components of the polymer coating apparatus 10 of FIGS. 1–4, and are numbered accordingly. A single puller 89 can be used for the tandem polymer coating apparatus 86 . By using a tandem coating apparatus 86, multiple layers of polymer coating may be applied to a single elongate intracorporeal device 12 by drawing the elongate intracorporeal device 12 through the first and second polymer coating apparatus 87 and 88 in serial in a direction of extrusion indicated by arrow 91. Multiple coatings may be applied so as to be axially coextensive on the elongate intracorporeal device 12. Multiple coatings may also be applied to separate axial portions of an elongate intracorporeal device 12 or such that the multiple coatings overlap each other by a desired amount. Although FIG. 7 depicts a tandem coating apparatus 86 having two polymer coating apparatus 87 and 88 in serial, any desired number of polymer coating apparatus may be used.

Figure 8:
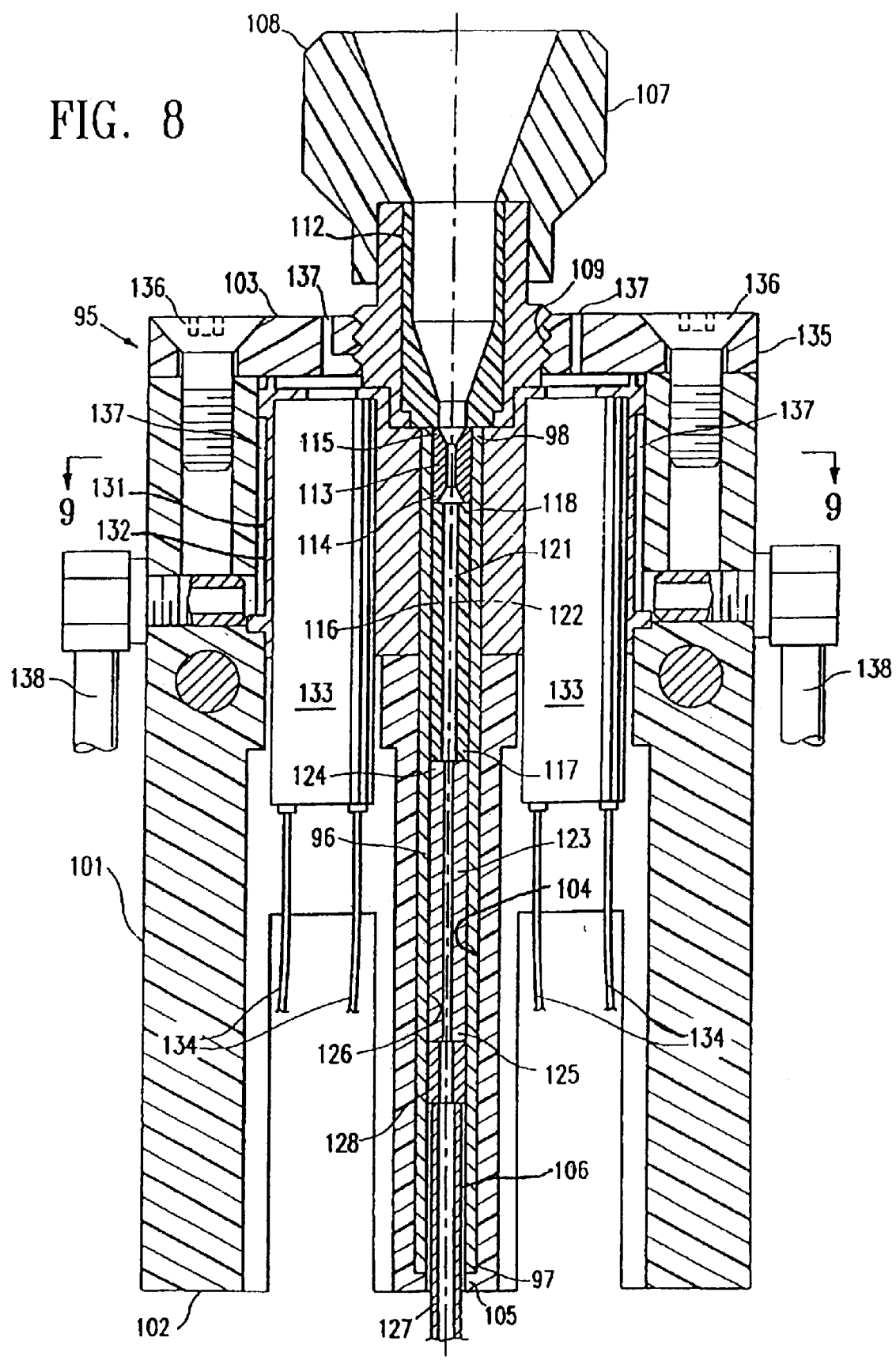
FIG. 8 illustrates an elevational view in section of a guide tube assembly having features of the invention.
Figure 9:
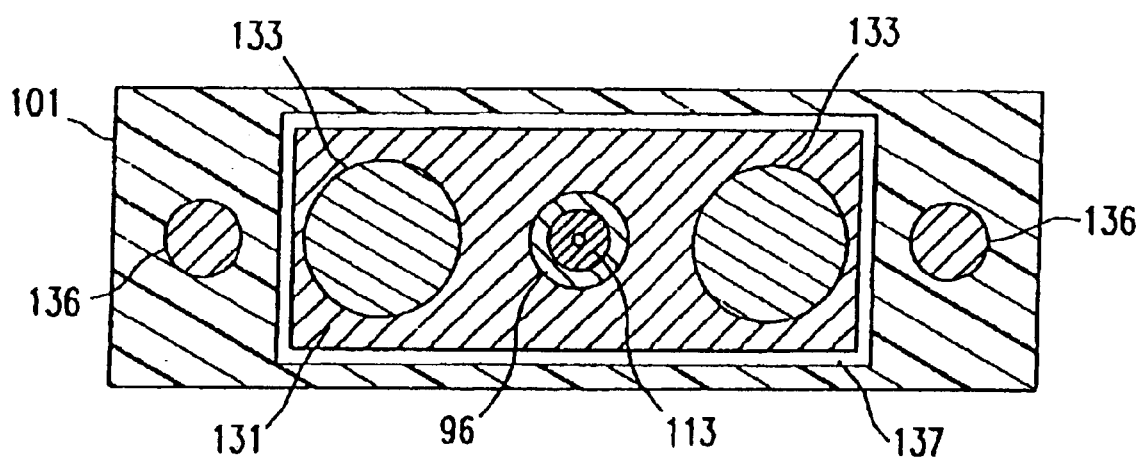
FIG. 9 is a transverse cross sectional view of the guide tube assembly of FIG. 8 taken along lines 9—9 in FIG. 8.

FIGS. 8 and 9 illustrate another embodiment of a guide tube assembly 95 having features of the invention. The guide tube assembly 95 includes a guide tube 96 having an input end 97 and an output end 98 disposed partially within a guide tube housing 101. The guide tube 96 can be made from a variety of polymer materials, specifically, high temperature polymer materials such as PI, PTFE, LCP and PEEK The guide tube housing 101 has an input end 102 and an output end 103 The guide tube housing 101 also has a central inner lumen 104 which is configured to accept the guide tube 96. The central inner lumen 104 of the guide tube housing 101 has a retainer lip 105 at the input end 102 of the guide tube housing 101 which is configured to prevent the guide tube 96 from exiting the input end 102 of the guide tube housing 101 without blocking or interfering with a guide chamber 106 disposed within the guide tube 96. The central inner lumen 104 of the guide tube housing 101 is capped at the output end 103 with a retainer cap 107. The retainer cap 107 has a retainer cap top 108, a threaded portion 109 and a retainer cap insert 112. The retainer cap 107, when secured to the guide tube housing 101, confines the output end 98 of the guide tube 96 within the central inner lumen 104 of the guide tube housing 101.

Disposed within the output end 98 of the guide tube 96 is a die 113 which has an input end 114 and an output end 115 and which can have the same configuration, dimensions and materials as the die 31 shown in FIGS. 5–6C. Disposed within the guide tube 96 adjacent the input end 114 of the die 113 is an extrudable polymer cartridge 116 having an input end 117 and an output end 118. An inner lumen 121 extends along a longitudinal axis 122 of the extrudable polymer cartridge 116. A push tube 123 having a contact end 124 and an actuator end 125 is disposed within a guide chamber 126 of the guide tube 96 with the contact end 124 adjacent the input end 117 of the extrudable polymer cartridge 116. A push tube actuator rod 127 with an actuator rod tip 128 is disposed partially within the guide chamber 126 with the actuator rod tip 128 disposed adjacent the actuator end 125 of the push tube 123.

A heater member 131 is disposed within the guide tube housing 101 about the output end 98 of the guide tube 96. The heater member 131 has a heater member housing 132, heater rods 133 and heater lead wires 134 which supply power to the heater rods 133. The heater member housing 132 can be made from stainless steel or any other suitable material which can withstand high temperatures. It may be desirable to use a material which readily conducts heat for the heater member housing 132. The heater member 131 is held in place within the guide tube housing 101 by a guide tube housing cap 135 disposed at the output end 103 of the guide tube housing 101.

The guide tube housing cap 135 can be secured to the guide tube housing 101 by screws 136. The guide tube housing 101 has cooling air channels 137 disposed within the housing 101 fed by air lines 138 to allow air to be circulated about the heater member 131 and cool the heater member 131 after a polymer coating process has been completed. Thereafter, a new guide tube 96, die 113, extrudable polymer cartridge 116 and push tube 123 can be inserted into the guide tube assembly 95. The optionally disposable components of the guide tube assembly 95 including the guide tube 96, die 113, extrudable polymer cartridge 116 and push tube 123 may be replaced separately, or all at once as a modular subassembly.

The guide tube 96, die 113, extrudable polymer cartridge 116 and push tube 123 are replaced by removing the retainer cap 107, withdrawing the spent guide tube 96, die 113, extrudable polymer cartridge 116 and push tube 123, and then replacing a new guide tube, die, extrudable polymer cartridge and push tube. The retainer cap 107 is then secured to the guide tube housing 101. The guide tube housing 101, guide tube housing cap 135 and retainer cap top 108 can all be made from a high strength machineable polymer insulator, such as Vespel® which is a polyimide resin based composite, or any other suitable material. An insulative material can be used for the guide tube housing 101, guide tube housing cap 135 and retainer cap top 108 in order to facilitate handling by the operators of the device who must handle the various components of the polymer coating apparatus during its operation.

The guide tube assembly 95 shown in FIGS. 8 and 9 is used in a manner similar to that discussed above with regard to the embodiment of the guide tube assembly 13 shown in FIGS. 1–4. The coating process parameters discussed above with regard to the embodiment of the guide tube assembly 13 shown in FIGS. 1–4, including, but not limited to, temperatures, pull speeds, rates of feed, forces on the extrudable polymer cartridge 57, and the like, and structures and alternative structures used to implement those parameters, can all be the same or similar for the embodiment of the guide tube assembly 95 shown in FIGS. 8 and 9.

FIGS. 10–19 illustrate various configurations of extrudable polymer cartridges having features of the invention. Specifically, FIGS. 10 and 11 illustrate an extrudable polymer cartridge 141 having an input end 142, an output end 143, and a plurality of longitudinal segments 144 which may be made of polymers having different compositions. Polymer composition of the longitudinal segments 144 may vary in material type, shore hardness, color, radiopaque doping concentrations and the like. An inner lumen 145 extends from the input end 142 to the output end, 143 and is concentric with a longitudinal axis 145A of the extrudable polymer cartridge 141. The extrudable polymer cartridge 141 can be molded with the longitudinal segments 144 molded into place adjacent each other. Alternatively, the longitudinal segments 144 could be molded or extruded separately, and subsequently bonded or fused together. Also, the longitudinal segments 144 could be molded or extruded separately and put into a guide chamber 28 or 126 of the invention without being bonded or fused together.

As used herein, the term polymer, as used with regard to polymer coatings, cartridges and the like, is intended to be interpreted broadly and include all polymers, prepolymers and the like which are suitable for use as a coating of an elongate intracorporeal device. Some materials suitable for the extrudable polymer cartridge 141, and all extrudable polymer cartridges discussed herein, can include polyurethanes, including polyurethane thermoplastic elastomers; polyamides (nylons); polyethers; polyesters; polyacetals; acrylics; methacrylics; cellulosics; fluoropolastics; epoxies; keton-based resins and polymers; polyimide based resins and polymers; bismaleimides; nitriles; polyarylates; polycarbonates; liquid crystal polymers; terephthalate resins and polymers including polybutylene terephthalate and polyethylene terephthalate; polyetherimides; polyolefins including polyethylenes, polypropylenes, polybutylenes, polybutadienes; polyvinyls including polystyrenes and polyvinyl chlorides; elastomers especially thermoplastic elastomers; silicones; rubbers; ionomers; ceramers; dendritic polymers; and derivatives, copolymers, multipolymers, blends and/or mixtures of any of the previous listed resins and polymers within each group and between each group. This latter includes polyether block amide elastomers such as COPA and PEBAX.

Any of the aforementioned polymers may be loaded with additives to control the physical properties such as flexural modulus, hardness, and radiopacity. The shore hardness of an embodiment of extrudable polymer cartridge 141 and embodiments of other extrudable polymer cartridges discussed herein can range from about 50A to about 55D, preferably about 80A to about 50D, and more preferably about 85A to about 95A.

FIGS. 12 and 13 show an extrudable polymer cartridge 146 having an input end 147, an output end 148, a first lateral segment 149 and a second lateral segment 150. An inner lumen 151 extends from the input end 147 to the output end 148 and is concentrically located within the extrudable polymer cartridge 146. The extrudable polymer cartridge 146 can be formed by molding or extruding the cartridge 146 in its final form. In addition, the first and second lateral segments 149 and 150 could be formed independently and then fused or bonded together, or placed within a guide chamber 28 or 126 of the invention together without being fused or bonded together.

FIGS. 14 and 15 illustrate an extrudable polymer cartridge 153 having an input end 154 and an output end 155 with an inner lumen 156 extending from the input end 154 to the output end 155. The inner lumen 156 has a longitudinal axis 157 which is substantially parallel to a longitudinal axis 158 of the extrudable polymer cartridge 153 and laterally offset from the longitudinal axis 158 of the extrudable polymer cartridge 153.

FIGS. 16 and 17 show an extrudable polymer cartridge 161 having an input end 162 and an output end 162. The extrudable polymer cartridge 161 has a first concentric layer 164 and a second concentric layer 165 disposed about the first concentric layer 164. An inner lumen 166 extends from the input end 162 to the output end 163 and is disposed concentrically within the extrudable polymer cartridge 161. The first concentric layer 164 may have a different polymer composition from the second concentric layer 165.

FIGS. 18 and 19 show an extrudable polymer cartridge 167 having an input end 168 and an output end 169. A first inner lumen 170 extends from the input end 168 to the output end 169 which may be disposed substantially concentric within the extrudable polymer cartridge 167 and which is substantially parallel to a longitudinal axis 171 of the extrudable polymer cartridge. A second inner lumen 172 extends from the input end 168 to the output end 169 and is also substantially parallel to the longitudinal axis 171 of the extrudable polymer cartridge 167. The second inner lumen 172 has a longitudinal axis 173 which is offset from the longitudinal axis 171 of the extrudable polymer cartridge 167. The first inner lumen 170 would can encompass an elongate intracorporeal device during an extrusion process. The second inner lumen 172 could be used to encompass a secondary elongate element such as a wire, fiberoptic, small diameter tubing or the like. The use of such an extrudable polymer cartridge 167 would facilitate application of a polymer coating to a plurality of elongate members which could be drawn through guide chambers 28 or 126 and extrusion orifice 68 during a coating process.

Unless otherwise described herein, conventional materials and manufacturing methods may be used to make the guiding members of the present invention. Additionally, various modifications may be made to the present invention without departing from the scope thereof. While particular forms of the invention have been illustrated and described, it will be apparent that various modifications can be made without departing from the spirit and scope of the invention. Accordingly, it is not intended that the invention be limited, except as by the appended claims.

What is claimed is:

1. A method for coating an elongate intracorporeal medical device, comprising:
   providing a chamber having a die at one end with an orifice and an input port at another end;
   providing a solid polymer cartridge having a lumen therein inside the chamber;
   passing the elongate intracorporeal medical device through the input port, lumen and orifice;
   compressing the polymer cartridge against the die;
   heating the polymer cartridge; and
   advancing the elongate intracorporeal medical device through the orifice.

2. The method of claim 1, wherein the polymer cartridge includes radiopaque doping.

3. The method of claim 1, wherein the polymer cartridge includes a plurality of longitudinal segments including different materials.

4. The method of claim 1, wherein the polymer cartridge includes a plurality of concentric layers including different materials.

5. The method of claim 1, wherein the intracorporeal medical device is simultaneously pushed and pulled through the orifice.

6. The method of claim 1, wherein the polymer cartridge includes a tubular shape that is split radially at least into halves.

7. A method for coating a guide wire, comprising:
   providing a chamber having a die at one end with an orifice and an input port at another end;
   providing a solid polymer cartridge having a lumen therein inside the chamber;
   passing the guide wire through the input port, lumen, and orifice;
   compressing the polymer cartridge against the die;
   concurrently extruding the polymer cartridge through the orifice and advancing the guide wire through the orifice; and
   heating the polymer cartridge.

8. The method of claim 7, wherein the polymer cartridge is heated only proximate to the orifice.

9. The method of claim 7, wherein the guide wire is advanced at a rate of about 0.05 to about 1.0 cm/sec.

10. The method of claim 7, wherein the polymer cartridge is heated from about 340 to about 390 degrees Fahrenheit.

11. The method of claim 7, wherein compressing the polymer cartridge is achieved by a force of about 0.5 to about 10 pounds.

12. The method of claim 7, wherein the die includes a high temperature polymer.

13. The method of claim 7, wherein compressing the polymer cartridge is achieved by a constant force.

14. The method of claim 7, wherein the die includes an inner lumen leading to the orifice having a length of about 0.02 to about 0.5 inch.

15. A method for coating a guide wire, comprising:
   providing a chamber having a die at one end with an orifice and an input port at another end;
   providing a solid polymer cartridge;
   passing the guide wire through the input port and orifice;
   disposing the polymer cartridge adjacent to the guide wire;
   compressing the polymer cartridge against the die;
   concurrently extruding the polymer cartridge through the orifice and advancing the guide wire through the orifice; and
   heating the polymer cartridge.

16. The method of claim 15, wherein passing the guide wire through the input port and orifice, disposing the polymer cartridge adjacent to the guide wire, compressing the polymer cartridge against the die, concurrently extruding the polymer cartridge through the orifice and advancing the guide wire through the orifice, and heating the polymer cartridge are repeated to produce a plurality of at least partially overlying coatings.

17. The method of claim 15, wherein the polymer cartridge includes an additive to affect at least one of flexural modulus, hardness, and radiopacity of the coating.

18. The method of claim 15, wherein heating the polymer cartridge includes at least one of softening and melting the polymer cartridge in a melt zone proximate to the die.

19. The method of claim 15, wherein the die includes an input taper and an output taper on opposite sides of the orifice.

20. The method of claim 15, wherein heating the polymer cartridge includes creating a temperature gradient longitudinally along the chamber.

* * * * *

UNITED STATES PATENT AND TRADEMARK OFFICE
CERTIFICATE OF CORRECTION

PATENT NO. : 6,733,819 B2
DATED : May 11, 2004
INVENTOR(S) : David Burkett and Emmanuel Biagtan It is certified that error appears in the above-identified patent and that said Letters Patent is hereby corrected as shown below:

Column 1,
Line 51, delete "Nell" and insert -- well --.

Column 9,
Line 44, after "material" insert -- . -- (a period).

Column 10,
Line 32, after "PEEK" insert -- . -- (a period).
Line 34, after "103" insert -- . -- (a period).

Column 11,
Line 60, after "output end" delete ",".

Signed and Sealed this

Thirtieth Day of November, 2004

JON W. DUDAS
*Director of the United States Patent and Trademark Office*